(12) United States Patent
Flint et al.

(10) Patent No.: US 11,565,132 B2
(45) Date of Patent: Jan. 31, 2023

(54) METHOD FOR USE WITH A RADIOTHERAPY DEVICE

(71) Applicant: Elekta Limited, Crawley (GB)

(72) Inventors: Chris Flint, Crawley (GB); Keith Richardson, Crawley (GB); Marcelo Jordao, Crawley (GB); Mark Holmes, Crawley (GB); Alessandra Chiap, Crawley (GB)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 17/250,654

(22) PCT Filed: Aug. 16, 2019

(86) PCT No.: PCT/EP2019/072063
§ 371 (c)(1),
(2) Date: Feb. 16, 2021

(87) PCT Pub. No.: WO2020/035615
PCT Pub. Date: Feb. 20, 2020

(65) Prior Publication Data
US 2021/0299478 A1    Sep. 30, 2021

(30) Foreign Application Priority Data
Aug. 16, 2018    (GB) .................................. 1813397

(51) Int. Cl.
*G08B 5/22* (2006.01)
*A61N 5/10* (2006.01)
(Continued)

(52) U.S. Cl.
CPC .......... *A61N 5/1075* (2013.01); *A61N 5/1081* (2013.01); *G01M 3/2846* (2013.01);
(Continued)

(58) Field of Classification Search
CPC . A61N 5/1075; A61N 5/1081; G01M 3/2846; G08B 5/22; G08B 21/187;
(Continued)

(56) References Cited

U.S. PATENT DOCUMENTS

| 2014/0266208 A1 | 9/2014 | Dempsey et al. |
| 2018/0279461 A1* | 9/2018 | Agustsson ............. H05H 9/048 |
| 2019/0070437 A1* | 3/2019 | Olcott .................. A61N 5/1081 |

FOREIGN PATENT DOCUMENTS

| CN | 101966369 B | 12/2011 |
| CN | 203015264 U | 6/2013 |

(Continued)

OTHER PUBLICATIONS

"International Application Serial No. PCT/EP2019/072063, International Search Report dated Dec. 5, 2019", (dated Dec. 5, 2019), 4 pgs.

(Continued)

*Primary Examiner* — Hongmin Fan
(74) *Attorney, Agent, or Firm* — Schwegman Lundberg & Woessner, P.A.

(57) ABSTRACT

Disclosed herein is a method of determining the nature of a fault in a radiotherapy device comprising a linear accelerator. The radiotherapy device is configured to provide therapeutic radiation to a patient. The radiotherapy device comprises a vacuum tube comprising an electron gun, a waveguide configured to accelerate electrons emitted by the electron gun toward a target to produce said radiation, and a flight tube. The electron gun is located at a first end of the vacuum tube and the flight tube is located at a second end of the vacuum tube. The radiotherapy device further comprises a first and a second sensor. The first sensor is configured to provide signals indicative of pressure at a first region inside the vacuum tube and the second sensor is configured to provide signals indicative of pressure at a second region (Continued)

inside the vacuum tube. The first region is closer to the first end of the vacuum tube than the second region is. The method comprises processing a first value derived from signals from the first sensor and a second value derived from signals from the second sensor. The first value is indicative of pressure at the first region inside the vacuum tube, and the second value is indicative of pressure at the second region inside the vacuum tube. Processing the first and second value comprises comparing the first value with a first threshold and comparing the second value with a second threshold; and, based on the processing of the signals, determining that the nature of the fault is associated with the flight tube.

11 Claims, 10 Drawing Sheets

(51) Int. Cl.
*G01M 3/28* (2006.01)
*G08B 21/18* (2006.01)
*H05H 7/22* (2006.01)
*H05H 9/00* (2006.01)

(52) U.S. Cl.
CPC ............. *G08B 5/22* (2013.01); *G08B 21/187* (2013.01); *H05H 7/22* (2013.01); *H05H 9/00* (2013.01)

(58) Field of Classification Search
CPC ........ H05H 7/22; H05H 9/00; H05H 2277/11; H05H 9/02; H05H 9/048
See application file for complete search history.

(56) References Cited

FOREIGN PATENT DOCUMENTS

| | | |
|---|---|---|
| JP | 2013235706 A | 11/2013 |
| WO | WO-2010085723 A1 | 7/2010 |

OTHER PUBLICATIONS

"International Application Serial No. PCT/EP2019/072063, Written Opinion dated Dec. 5, 2019", (dated Dec. 5, 2019), 7 pgs.
"United Kingdom Application Serial No. 1813397.5, Examination Report dated Jan. 30, 2019", (dated Jan. 30, 2021), 5 pgs.
Bhattacharjee, D., et al., "The UHV system of the 10 MeV RF electron linac", Journal of Physics: Conference Series. vol. 114. No. 1. IOP Publishing, (2008), 5 pgs.

\* cited by examiner

METHOD FOR USE WITH A RADIOTHERAPY DEVICE

PRIORITY APPLICATIONS

This application is a U.S. National Stage Filing under 35 U.S.C. § 371 from International Application No. PCT/EP2019/072063, filed on Aug. 16, 2019, and published as WO2020/035615 on Feb. 20, 2020, which claims the benefit of priority to United Kingdom Application No. 1813397.5, filed on Aug. 16, 2018; the benefit of priority of each of which is hereby claimed herein, and which applications and publication are hereby incorporated herein by reference in their entirety.

This disclosure relates to the field of remote diagnostics, and in particular to a method of identifying the nature of a fault in a radiotherapy device performing sub-optimally.

BACKGROUND

Radiotherapy devices are an important tool in modern cancer treatment. Radiotherapy devices are large, complex machines, with many moving parts and inter-operating mechanisms. Despite precision engineering and rigorous testing, some component parts of a radiotherapy machines may start to degrade over the lifetime of the machine. This can sometimes lead to sub-optimal operation and even the occasional safety override.

If at any point during treatment a radiotherapy device starts to function outside of its normal operating parameters, a safety override or "interrupt" occurs, whereby the machine stops delivering radiation to ensure patient safety. Such an event is inconvenient, as it adds time to the treatment, and in some cases means the treatment session must finish prematurely. Unplanned equipment downtime can disrupt planned treatment schedules, and may be expensive for the owner, be it due to loss of revenue, servicing and repair costs, or both.

It has been surmised that, as with other industries, predictive maintenance and/or remote diagnostic techniques could be applied to radiotherapy machines. However, given the complexity of the machines and the sheer volume of data which may be gathered during operation, it is difficult to know how to analyse any available data to inform the predictive maintenance techniques. For example, while particular data patterns may be indicative of a particular fault, identifying the link between particular data patterns and the particular fault is often non-intuitive even for experienced service engineers. Even when a problematic machine is identified, trying to ascertain the nature of the fault is very difficult given the abundance of data and the complex interrelationships between the various components of the machine. In other words, even if a wealth of data from a radiotherapy device is available, successfully determining the nature of a fault is not a trivial matter.

The present invention seeks to address these and other disadvantages encountered in the prior art by providing a method of identifying, preferably remotely, the nature of a fault in a radiotherapy device, for example a device which is performing sub-optimally.

SUMMARY

An invention is set out in the independent claims. Optional features are set out in the dependent claims.

FIGURES

Specific embodiments are now described, by way of example only, with reference to the drawings, in which.

DETAILED DESCRIPTION

Figure 1:
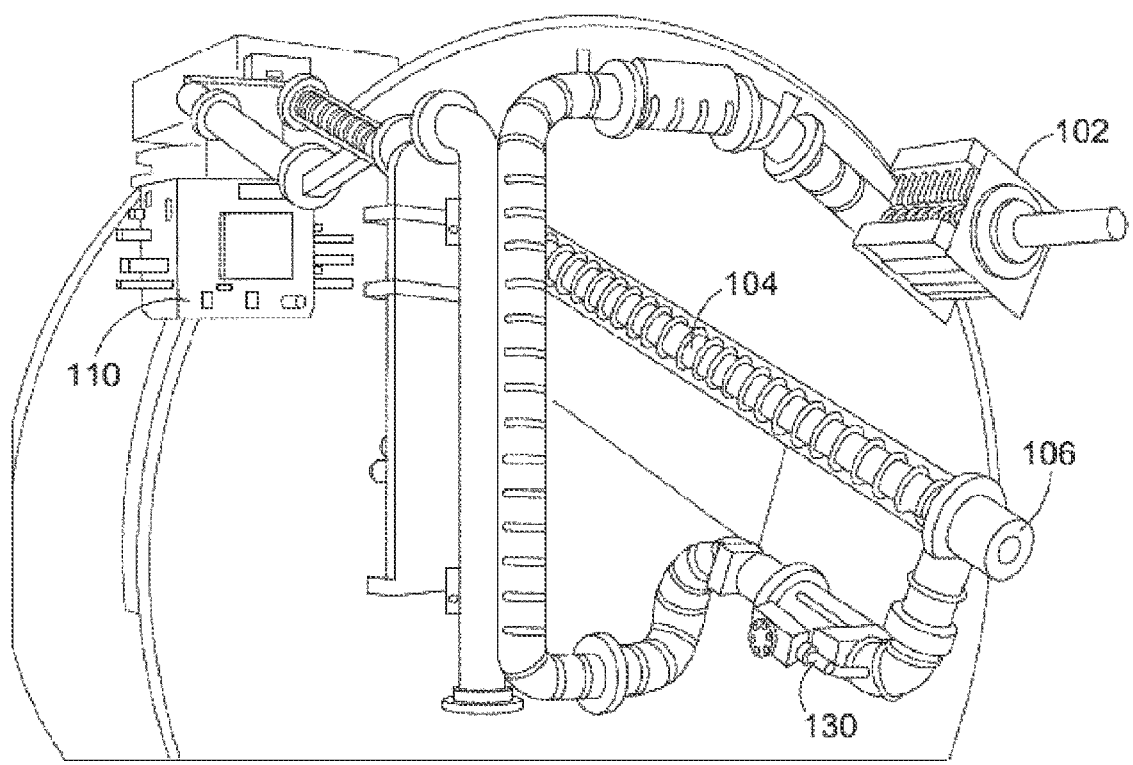
FIG. 1 depicts a schematic illustration of a LINAC device.

The present disclosure relates to a method of determining the nature of a fault in a radiotherapy machine or device. The device may be suitable for delivering a beam of radiation to a patient in order to treat a tumour. An example of a radiation source for producing a beam is a linear accelerator (LINAC). Clinical LINAC devices are configured to deliver high energy radiation to a patient.

Radiotherapy machines are beginning to be configured to produce and record a large amount of data as they operate; for example radiotherapy machines are configured to provide sensor readings from a variety of different sensors. These sensors produce data which can be stored in a database. Radiotherapy devices may also be configured to allow remote connection, enabling service engineers to access a wealth of information about any connected machine without having to travel to the site where the machine is located. It is expected that, in many cases, machines may be returned to optimal performance without an engineer ever having to physically interact with the machine. However, there will still be occasions where the fault cannot be fixed remotely, and an engineer must be sent to: inspect the machine; determine the nature of the fault; and perform any maintenance required. If the repair involves replacing a part, further machine downtime is required before the machine can be brought back online.

The present methods involve evaluating the condition and/or performance of radiotherapy equipment during its operation in order to identify, preferably remotely, the nature of a fault in a radiotherapy device which is performing sub-optimally. Such techniques are advantageous as they allow a manufacturer or maintenance service provider to attend the machine knowing what will be required to fix the machine prior to arrival. The disclosed techniques can help to reduce machine downtime and thereby minimise disruption to the machine's normal operation. The disclosed techniques can also be used to more effectively plan machine downtime for times which are more convenient or cost-effective for the owner of the equipment and/or the patients.

One potential fault in a LINAC device relates to a reduced quality of vacuum in the vacuum tube of the LINAC. This may, for example, be caused by a leak in one of the components which comprise the vacuum tube or vacuum pump system. Leaks in a vacuum tube of the LINAC negatively affect the quality of the vacuum in the vacuum tube, meaning electrons may be impeded to a greater degree as they propagate through the vacuum tube. This in turn can negatively impact beam quality. Leaks can develop for a number of reasons and in a variety of regions in the vacuum tube. The vacuum quality can be monitored as part of safety and quality control procedures to ensure that, if the quality of vacuum dips below a certain level, a safety override or interrupt occurs.

As will be discussed below, a potential cause of a reduced quality of vacuum in the vacuum tube is a leak in the flight tube. Such leaks may be caused, for example, by small 'pinholes' on the target window which form as the LINAC operates. Machines where the fault is of this nature have variable performance, and given the large amount of possible causes of a reduced quality of vacuum it is extremely difficult to determine the nature of the fault. It is possible that it is not known that the vacuum is the cause of the machine operating sub-optimally. Machines with flight tube related faults often have machine output fluctuations, and so a field service engineer investigating the fault may incorrectly conclude that the sub-optimal performance of the machine is due to, for example, a magnetron issue, rather than due to a fault with the flight tube. The present disclosure advantageously allows a determination that the nature of the fault is associated with the flight tube.

High-Level Overview of a LINAC

FIG. 1 depicts a LINAC suitable for delivering, and configured to deliver, a beam of radiation to a patient during radiotherapy treatment. In operation, the LINAC device produces and shapes a beam of radiation and directs it toward a target region within the patient's body in accordance with a radiotherapy treatment plan.

A medical LINAC machine is by necessity complex, with many inter-operating component parts. A brief summary of the operation of a typical LINAC will be given with respect to the LINAC device depicted in FIG. 1, which comprises a source 102 of radiofrequency waves, a waveguide, a source of electrons, a system capable of creating a strong vacuum comprising one or more vacuum pumps 130, a heavy metal target which produces X-rays when hit by an electron beam, and a complex arrangement of magnets capable of redirecting and focusing the electron beam onto the target. The device depicted in FIG. 1 also comprises a treatment head which houses various apparatus configured to, for example, collimate and shape the resultant X-ray beam.

The source 102 of radiofrequency waves, such as a magnetron, produces radiofrequency waves. The source 102 of radiofrequency waves is coupled to the waveguide 104, and is configured to pulse radiofrequency waves into the waveguide 104. Radiofrequency waves pass from the source 102 of radiofrequency waves through an RF input window and into a RF input connecting pipe or tube. The RF input connecting pipe or tube is coupled with the waveguide, and may join the waveguide at a substantially 90° angle as shown in FIG. 1. The connecting tube or pipe may join the waveguide via a so-called 'elbow joint' or 't-shaped joint'. A source 106 of electrons, such as an electron gun, is coupled to the waveguide 104 and is configured to inject electrons into the waveguide 104. In the source 106 of electrons, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source 106 and the waveguide 104 is such that the radiofrequency waves accelerate the electrons to very high energies as they propagate through the waveguide 104. The design of the waveguide 104 depends on whether the LINAC accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104.

As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they pass into a flight tube. The flight tube may be connected to the waveguide by a connecting tube. This connecting tube or connecting structure may be called a drift tube. The drift tube also forms part of the vacuum tube. RF waves exit the waveguide via an RF output connecting pipe or tube coupled with the drift tube. As with the RF input pipe which introduces RF to the waveguide, the pipe or tube through which RF exits the waveguide connects to the vacuum tube via an elbow joint or 'T-shaped' joint. RF passes out from the vacuum system via an RF output window which seals the vacuum system.

The flight tube is kept under vacuum conditions by the pump system. The electrons travel along a slalom path toward the heavy metal target. The target may comprise, for example, tungsten. Whilst the electrons travel through the flight tube, an arrangement of focusing magnets act to direct and focus the beam on the target. The slalom path allows the overall length of the LINAC to be reduced while ensuring that the beam of accelerated electrons, which is comprised of electrons with a small spread of energies, is focused on the target.

To ensure that propagation of the electrons is not impeded as the electron beam travels toward the target, the waveguide 104 is evacuated using a vacuum system comprising a vacuum pump 130 or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104. Together, the electron gun 106, waveguide 104 and the flight tube form a vacuum tube in which electrons can be accelerated and directed toward a target in vacuum conditions. In implementations comprising a drift tube connecting the waveguide 104 to the flight tube, the drift tube also forms part of the vacuum tube. The vacuum tube has two ends. The ends may be described as opposing ends. The electron gun 106 is located at a first end of the vacuum tube and the flight tube is located at a second end of the vacuum tube. In other words, the flight tube is located at a distal end of the waveguide 104, and hence vacuum tube, from the electron gun 106.

The combination of the components kept under vacuum, e.g. the vacuum tube and any connecting pipes and tubes, for example those connecting tubes and pipes which couple the RF input and output windows to the vacuum tube and the internal volume of the pumps, may be referred to as the vacuum system. The vacuum system is sealed and is constantly kept under vacuum. To produce the necessary high vacuum conditions, the vacuum system may undergo several stages of pumping before the high quality vacuum may be maintained using e.g. ion pumps. For example, first, a normal piston-based pump may be used, followed by a stage wherein the pressure inside the vacuum system is further lowered using a turbo-molecular pump. Finally, ion pumps are used to ensure the system is kept at ultra-low pressure.

When the high energy electrons hit the target, X-rays are produced in a variety of directions. The target is located inside the flight tube, and is located at the end of the flight tube to seal the vacuum system. The flight tube also comprises a target window, which is transparent to X-rays, which is positioned to allow the X-rays which are produced when the LINAC is in operation to pass from the evacuated flight tube through the target window and into the treatment head 110. At this point, a primary collimator blocks X-rays travelling in certain directions and passes only forward travelling X-rays to produce a cone shaped beam. The X-rays are filtered, and then pass through one or more ion chambers for dose measuring. The beam can be shaped in various ways by beam-shaping apparatus, for example by using a multi-leaf collimator, before it passes into the patient as part of radiotherapy treatment.

In some implementations, the LINAC is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the LINAC. In essence, it is possible to swap between the first and second mode by moving the heavy metal target in or out of the electron beam path and replacing it with a so-called 'electron window'. The electron window is substantially transparent to electrons and allows electrons to exit the flight tube.

The end of the flight tube may be sealed by a component which comprises both a target and an electron window. It is then possible to swap between the first and second mode by moving the flight tube such that the electron beam points toward either the target or the electron window. The drift tube, which connects the waveguide to the start of the flight tube, is therefore slightly flexible to allow the flight tube to move. In other words, the flight tube will move when the user changes between using an electron and XRay energy, this puts either the tungsten target (XRAY) or electron window (Electron) in position to treat.

The LINAC device also comprises several other components and systems. The whole system is cooled by a water cooling system (not shown in the figures). The water cooling system may be used, in particular, to cool the waveguide 104, target, and radiofrequency source 102. In order to ensure the LINAC does not leak radiation, appropriate shielding is also provided. As will be understood by the person skilled in the art, a LINAC device used for radiotherapy treatment will have additional apparatus such as a gantry to support and rotate the LINAC, a patient support surface, and a controller or processor configured to control the LINAC apparatus.

Details of Apparatus and Sensors—Case Specific

Figure 2:
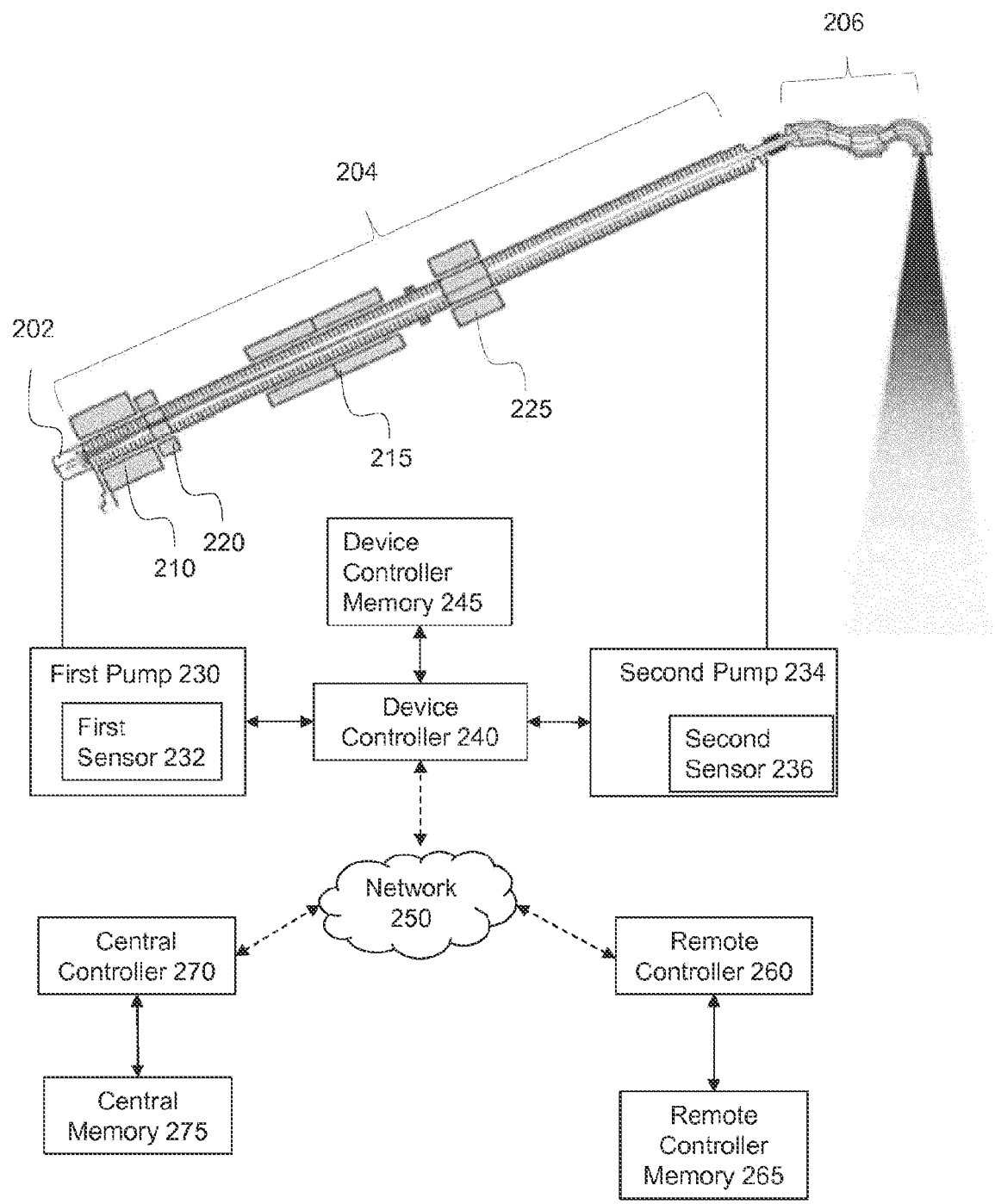
FIG. 2 depicts a cross-section through the vacuum tube of the LINAC device of FIG. 1.

FIG. 2 depicts a cross-section through a vacuum tube of a LINAC. As detailed above, the vacuum tube is comprised of an electron gun 202, a waveguide 204, and a flight tube 206. The electron gun 202 is configured to inject electrons into the waveguide 204. In this example, the electron beam may be focused by a first arrangement of focusing magnets 210 and a second arrangement of focusing magnets 215. The beam is 'steered', i.e. directed, by a first arrangement of steering magnets 220 and a second arrangement of steering magnets 225. While the LINAC is in use, the electron gun 202, waveguide 204 and flight tube 206 are kept under high vacuum conditions by a vacuum system or suitable vacuum apparatus.

In the example of FIG. 2, the vacuum system comprises two pumps coupled to either end of the vacuum tube. The region of the vacuum tube to which the first pump 230 is coupled is arranged at an opposing end of the vacuum tube to the region of the vacuum tube to which the second pump 234 is coupled. The first pump 230 is coupled with a first end of the vacuum tube at which the electron gun 202 is located. The first pump 230 may be coupled with the area of the vacuum tube adjacent the electron gun, i.e. adjacent where the electron gun 202 injects electrons into the waveguide 204. The first pump 230 is arranged and configured to remove gas molecules from the vacuum tube, and in particular is arranged and configured to remove gas molecules primarily from a first region of the vacuum tube. The first region may comprise the volume of the tube occupied by the electron gun and/or a region of the vacuum tube proximate the electron gun. The region of the vacuum tube proximate the electron gun may be described as being adjacent to or next to the electron gun. The second pump 234 is coupled with a second region of the vacuum tube located at a second end of the vacuum tube at which the flight tube 236, and hence the target, is located. The second pump 234 may be coupled with the flight tube 206 itself. The second pump 234 is arranged and configured to remove gas molecules from the vacuum tube, and in particular is arranged and configured to remove gas molecules primarily from a second region of the vacuum tube. The second region may comprise the flight tube 206 itself and/or a region of the vacuum tube proximate the flight tube 206. The region of the vacuum tube proximate the flight tube may be described as being adjacent to or next to the flight tube. For example, the second pump 234 may be coupled with the vacuum tube in a connecting region intermediate the waveguide 204 and the flight tube 206.

In an implementation, the gun pump is connected to a tube or pipe which joins the source of radiofrequency waves with the waveguide. This connecting tube or pipe introduces RF to the waveguide and joins the waveguide at a region of the vacuum tube via an elbow joint. In other words, the RF input connecting pipe or tube joins the RF input window to the waveguide. Typically, the RF input connecting pipe or tube joins, or couples with, the waveguide at a region of the waveguide adjacent the electron gun.

Figure 6:
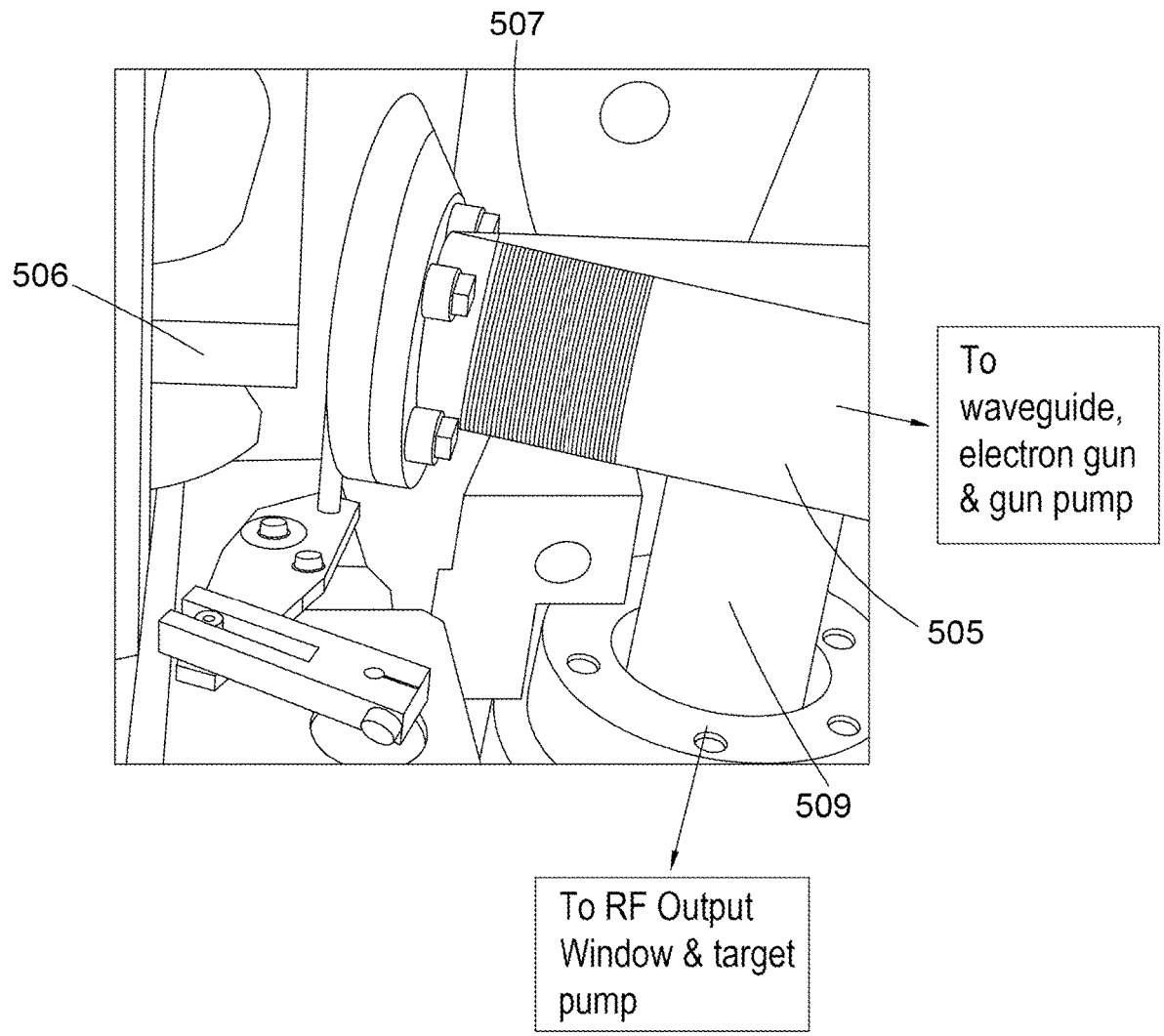
FIG. 6 depicts a region of a vacuum tube according to the present disclosure.

In an implementation, the target pump is connected to a tube or pipe through which RF exits the waveguide. This connecting tube or pipe couples a region of the waveguide with the RF output window. This RF output connecting pipe joins, or couples with, the waveguide at a region of the waveguide adjacent the flight tube, for example the drift tube. The RF input tube/pipe and the RF output tube/pipe couple with the vacuum tube via elbow joints or 'T-shaped' joints. This implementation is depicted in FIG. 6, which depicts a drift tube 507 positioned in between a waveguide (only a small part of which can be seen in the figure) and a flight tube 506 (only a small part of which can be seen in the figure). An 'elbow joint' 505 couples the drift tube 507 with an RF output connecting pipe 509 which terminates in an RF output window through which RF can exit the vacuum system. The target pump is coupled to a region of the RF exit connecting pipe between the elbow joint 505 and the RF exit window (not shown). Thus, the region of the vacuum tube to which the second pump coupled may be described as being adjacent to or next to the flight tube and/or approximate to or adjacent a drift tube which is coupled with the flight tube.

The first pump 230 may be described as being located near, or substantially near, the electron gun 202, and hence substantially near the location at which electrons enter the waveguide 204. The second pump 234 may be located near, or substantially near, the entrance to the flight tube 206, in which the target is located. The first pump 230 may therefore be referred to as a 'gun pump', and the second pump 234 may be referred to as a 'target pump'.

The first and second pumps act to create high vacuum conditions inside the electron gun 204, waveguide 206 and flight tube 206 and hence may be described as vacuum pumps. Suitable vacuum pumps include ion pumps such as diode and noble diode pumps. Ion pumps are capable of producing very low pressure inside the sealed volume of the vacuum tube. Other pumps capable of providing UHV conditions may also be used, including turbomolecular pumps and diffusion pumps.

No sensors are located inside the vacuum tube, i.e. the waveguide and flight tube, itself because there is very little space inside these components where such a sensor could be fitted. Also, any components placed inside the waveguide would affect the electromagnetic field inside the waveguide which is likely to have a negative impact on the acceleration of the electrons inside the waveguide. Further, components placed inside the vacuum tube at regions where electrons pass are susceptible to a lot of induced radiation which would not be desirable. Finally, any sensor placed inside the vacuum tube would be incredibly difficult to replace if it were to go faulty.

However, it is possible to obtain an indication of pressure inside the vacuum tube from readings provided by the vacuum pumps themselves. The readings from the pumps can be used to give an indication of the quality of the vacuum inside the vacuum tube. The first pump 230 comprises a first sensor 232 suitable for providing, and configured to provide, a signal indicative of a pressure inside the vacuum tube. As the first vacuum pump 230 is coupled with a portion of the vacuum tube substantially near the electron gun 202, the first sensor 232 is able to provide signals indicative of a pressure inside the vacuum tube proximate the electron gun 232. Thus the first sensor 232 signals may be referred to as the 'gun vacuum' signal or gun vacuum values.

Accordingly, broadly speaking the first sensor is configured to provide signals indicative of pressure at a first region inside the vacuum tube and the second sensor is configured to provide signals indicative of pressure at a second region inside the vacuum tube. The first and second regions are located at opposing ends of the vacuum tube. In other words, the first region is closer to the first end of the vacuum tube than the second region is, and it follows that the second region is closer to the second end of the vacuum tube than the first region is.

In a manner similar to the first pump 230 and the first sensor 232, the second vacuum pump 234 comprises a second sensor 236 suitable for providing, and configured to provide, a signal indicative of a pressure inside the vacuum tube. More specifically, the second sensor 206 is configured to provide signals indicative of a pressure inside the vacuum tube proximate the target and/or the flight tube 206. Thus signals from the second sensor 236 may be referred to as the 'target vacuum' signal or target vacuum values. More generally, the signals provided by the vacuum pumps via their respective sensors may be referred to as pressure signals. The sensors measure the pressure, i.e. vacuum level, of respective regions inside the first and second pumps. These regions are part of the same enclosed volume defined by the vacuum tube, and thus the first sensor is able to provide signals indicative of a pressure at the first end of the vacuum tube to which the first pump is coupled and the second sensor is able to provide signals indicative of a pressure at the second end of the vacuum tube to which the second pump is coupled.

The sensors may comprise any number of possible sensors which are suitable to measure vacuum pressure. Example sensors which may form part of a vacuum pump, and which may be used to provide signals indicative if pressure, include Pirani gauges and ionisation gauges. The vacuum pressure at the gun and target end is measured at the ion pump control unit (IPCU).

The first and second pump 230, 234 further comprise means with which to communicate with a device controller 240. For example, the pumps may comprise suitable processing circuitry and transmitting antennas. The first and second pump 230, 234 are electronically and/or communicatively coupled to a device controller 240. The device controller receives signals from both the first and second pump 230, 234 as generated, or produced, by the first and second sensors 232, 236. The device controller 240 is electronically and/or communicatively coupled to a device controller memory 245. The device controller 240 and device controller memory 245 may be configured to store signals generated by the first and second sensors 232, 236. The generated signals from the first and second sensors comprise sensor data.

The device controller 240 is communicatively coupled to a central controller 270, for example via a network 250. The device controller 240 is configured to transmit, i.e. send, the sensor data to the central controller 270 to be stored on the central controller memory 275. The central controller memory 275 may comprise a number of different servers as part of a cloud storage solution. The central controller may be communicatively coupled to a plurality of radiotherapy devices via network 250, each of which are configured to transmit signals to the central controller 270 to be stored on central memory 275. Central controller 270 is adapted and configured to process received signals and store them in a database. Processing the signals may comprise, for example, calculating and storing daily averages of particular sensor data.

The radiotherapy device has a variety of sensors, the signals/readings from which are communicated to the device controller 240. The signals may be stored in the device controller memory 245 and/or may be communicated via the network to the central controller 270. The data may be uploaded to the central controller 270 as it is generated, or may be stored on the device controller memory 245 in order to be uploaded as a batch upload, for example at regular time intervals. Alternatively, the data may be continuously gathered by the device controller 240, for example the sensor signals may be sampled every 4 seconds, and data is uploaded if the data shows a particular variance from the previously uploaded data point. In a specific implementation, the data points are uploaded when there is a change of +/−0.04, and the device controller looks for a new data item once every 4 seconds, and once every second while the LINAC is delivering radiation.

The data is stored in a database on central memory 275, which may comprise data from sensors, for example the data includes the quality of vacuum as denoted by signals from the first and second sensors 232, 236, the degree of rotation of the gantry, whether or not radiation is being delivered at a particular time and the dose rate and machine output as indicated by a dosimeter or monitor chamber, as well as the water temperature at various points around the water cooling system. This data is given to provide examples, and the skilled person will appreciate that a modern LINAC device may be configured to generate a wealth of data from a large variety of sensors.

The device controller 240 and central controller 270 are both also communicatively coupled to a remote controller 260. The remote controller 260 may access the central database, which stores information and data regarding a plurality of radiotherapy devices, through the database 250 and by using a suitable software platform. The remote controller 260 may also access the device controller 240 to obtain real-time information regarding a particular radiotherapy machine.

The device, central and remote controllers may each be described as a processor, computer, or computing device. The controllers may be connected (e.g., networked) to each other and/or to other machines in a Local Area Network (LAN), an intranet, an extranet, or the Internet. The controllers may each operate in the capacity of a server or a client machine in a client-server network environment, or as a peer machine in a peer-to-peer (or distributed) network environment. The controllers may each be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only two respective and single controllers are illustrated, the term "controller" shall also be taken to include any collection of machines (e.g., computers) that individually or jointly execute a set (or multiple sets) of instructions to perform any one or more of the methodologies discussed herein.

The approaches of the present disclosure may be embodied on one or more of the device controller memory and the remote controller memory, or any other computer-readable medium. The medium may be a non-transitory computer-readable medium. The computer-readable medium carries computer-readable instructions arranged for execution upon a processor so as to make the controller/processor carry out any or all of the methods described herein. The term "computer-readable medium" as used herein refers to any medium that stores data and/or instructions for causing a processor to operate in a specific manner. Such storage medium may comprise non-volatile media and/or volatile media. Non-volatile media may include, for example, optical or magnetic disks. Volatile media may include dynamic memory. Exemplary forms of storage medium include, a floppy disk, a flexible disk, a hard disk, a solid state drive, a magnetic tape, or any other magnetic data storage medium, a CD-ROM, any other optical data storage medium, any physical medium with one or more patterns of holes, a RAM, a PROM, an EPROM, a FLASH-EPROM, NVRAM, and any other memory chip or cartridge.

Figure 5:
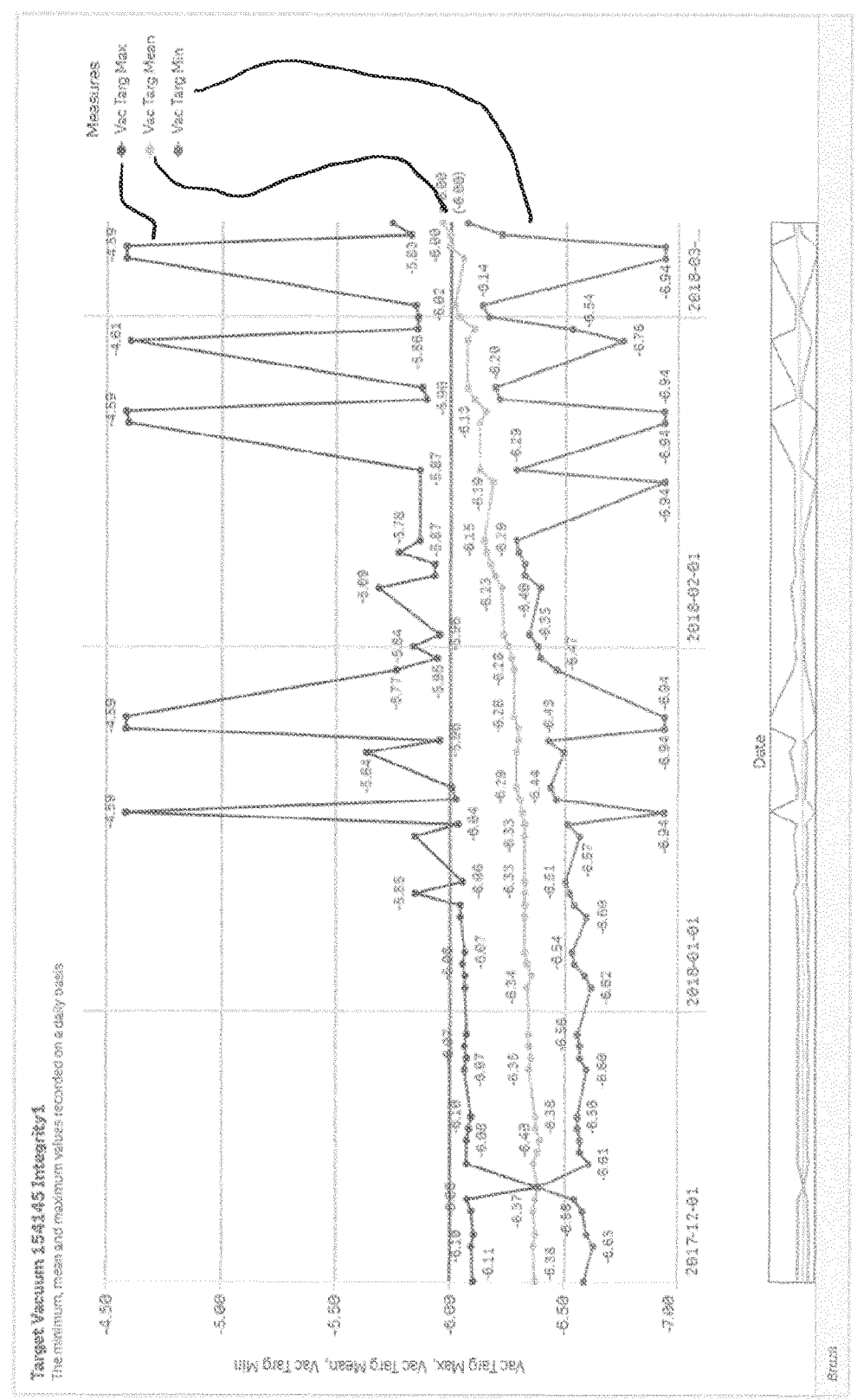
FIG. 5 depicts a graph showing vacuum values generated by a sensor according to the present disclosure.

FIG. 5 shows a graph generated using data from a database of sensor values as provided by sensors such as the sensors 232, 236 depicted in FIG. 2. The graph shows time along the X axis and pressure along the Y axis. The unit of the y axis is a semi-arbitrary unit which is derived from the vacuum pressure readings from each pump sensor. For a particular ion pump, the voltage of the ion pump is related to the $\log_{10}$ of the current absorbed by the pump as follows:

$$V_{rec-out} = 1.35 \cdot \log 10 I_{out} + 6.77$$

In an implementation, the vacuum pressure recorded on the ion pump control unit (IPCU) is then converted to give values between the range of −4.49 and −6.8, where −4.49 relates to a vacuum pressure of 1.55E-04 mBar and −6.8 is 5.60E-08 mBar. A reading of −5.50 is therefore 4.64E-06 mBar.

The graph shows signals received from the target vacuum pump as generated by the target vacuum sensor. The graph demonstrates the type of signals which may be received form the device controller and which may be accessible by a remote controller. A similar graph may be generated for the gun pump. The line which is generally uppermost on the graph is the target pump daily maximum reading. Each data point is the maximum value for a particular day, i.e. the maximum value for a particular data between a period from 00:00 to 23:59. The line which is generally lowermost on the graph is the target pump daily minimum reading, with each data point being the minimum value that day. Finally, the line which is generally between the maximum and minimum lines is the daily average line. Each data point on this line is the average target pump value for a particular day. In an implementation, it is this daily average value for each of the gun and target pump which is compared to first and second thresholds in order to determine whether a fault with the vacuum system is associated with the flight tube.

Specific Method

Figure 3:
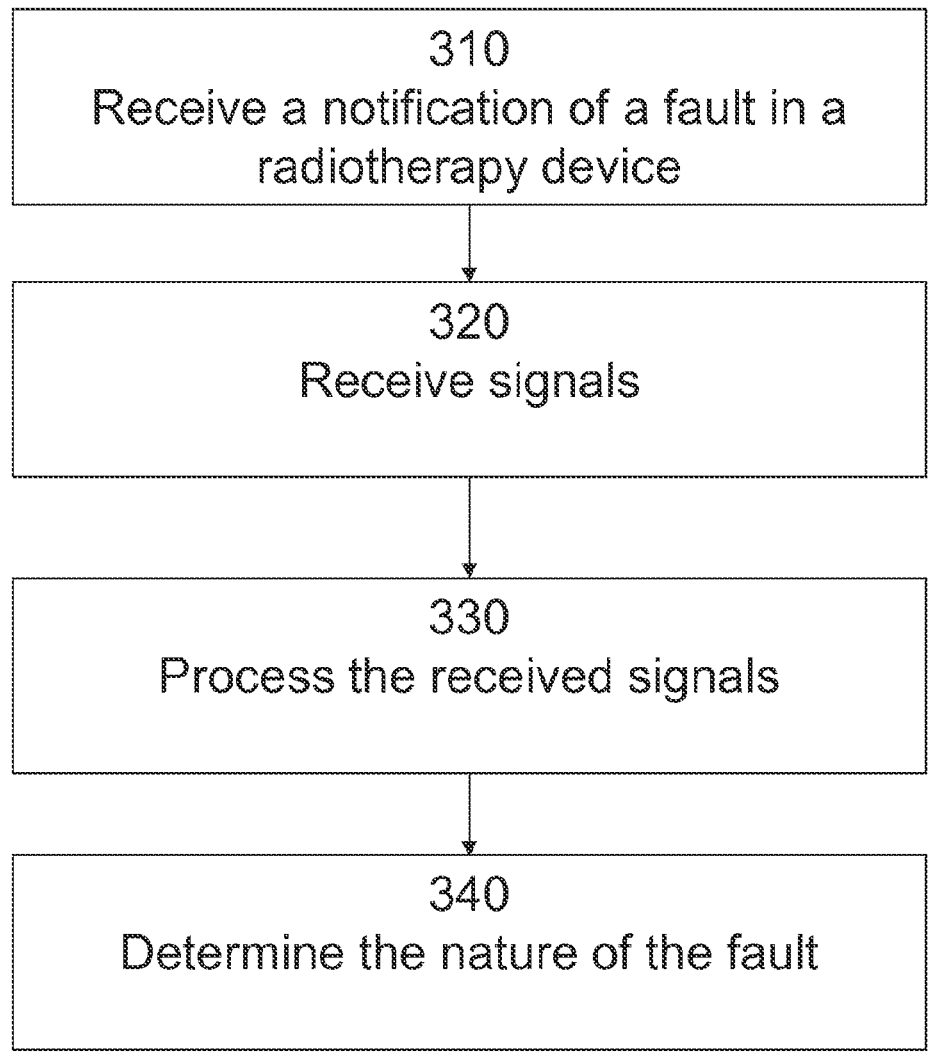
FIG. 3 depicts a method according to the present disclosure.

Reference is now made to the method depicted in the flowchart of FIG. 3. The method may begin from step 310 or step 320. Step 310 can therefore be considered as an optional step. At step 310, a notification is received of a fault in a radiotherapy device. The radiotherapy device may be a LINAC device. The notification may indicate that the radiotherapy device has begun operating outside of its normal operating parameters, however the nature, e.g. cause, of the fault is not known.

The device controller monitors signals/readings from a large variety of sensors and, if a reading falls below predetermined safety threshold or safety thresholds, i.e. the machine begins operating outside of its normal operating parameters, the device controller registers the fault in a database and may even initiate a safety override according to pre-programmed safety procedures.

The nature of the fault may be associated with the LINAC flight tube, for example the fault may be that the LINAC flight tube has a leak, for example a leak through one or more pinholes in the target window. This fault manifests itself by reducing the quality of the vacuum in the vacuum tube below optimal levels. The notification of a fault may indicate that the fault is with the vacuum tube, and/or is associated with the vacuum tube or pump system. However, beyond this information, at this stage the specific component giving rise to the fault is not known.

In an example where the nature of the fault is associated with the flight tube, the quality of the vacuum in the vacuum tube may be reduced below a fault threshold. The fault may be identified by comparing one or more of the first and second signals from the first and second pumps/sensors, or a combined signal such as an averaged signal from the first and second sensors 232, 236 with one or more fault thresholds. If one or both of the signals from the first and second sensors 232, 236 falls below a fault threshold, then the vacuum level and quality inside the vacuum tube is deemed to be non-optimal and a fault with the radiotherapy device is registered. The signals from the first and second sensors 232, 236 may be monitored by the device controller, and when a fault is registered the time of the fault as well as the sensor/pump which registered the fault may be stored in the device controller memory. This information is transmitted to the remote controller as a fault notification. When a fault is registered, the device controller may halt the operation of the radiotherapy device as part of a safety override process.

The notification may be triggered when one or more conditions are met. A possible condition that may cause a fault notification to be issued may be that a signal received from the first sensor or the second sensor has met or crossed a signal threshold. For example, the target vacuum signal may have fallen below a threshold value. In this instance, it has been found that an appropriate threshold value is a reading of −5.45 (5.60E-06 mBar), such that the target vacuum pressure signal falling below a reading of −5.45 (5.60E-06 mBar) causes a notification of a fault to be issued. The signals from both the gun and the target pumps are monitored and if either falls below a threshold, which may be a safety threshold or represent the vacuum being otherwise non-optimal, then a fault is registered. The device controller records from which pump the signals issued which caused the fault to be registered, e.g. the gun or the target pump.

At step 320, signals are received. This step may be undertaken in response to receiving the notification of a fault at step 310 or may be otherwise taken in order to begin the process of determining the nature of a fault. For example, the process can be manually started in response to an operator becoming aware that a radiotherapy machine has a fault. The signals are received from the first and second sensors 232, 236 associated with the first and second pumps 230, 234. As detailed elsewhere herein, the first and second sensor are configured to provide signals indicative of pressure inside the vacuum tube. More specifically, the first sensor is configured to provide signals indicative of a pressure inside the vacuum tube proximate the electron gun, and the second sensor is configured to provide signals indicative of a pressure inside the vacuum tube proximate the flight tube and/or the target. The first signals are processable to provide a first value indicative of pressure at the first end of the vacuum tube, and the second signals are processable to provide a second value indicative of pressure at the second end of the vacuum tube. The first value is derived from signals from the first sensor in any of the manners disclosed herein. Similarly, the second value is derived from signals from the second sensor in any of the manners disclosed herein.

The signals are received at one or more of the device controller and the remote controller. For example, the signals may be received at the device controller and stored in the device controller memory as part of a database/log of received signals from that particular radiotherapy machine. The device controller memory also stores a record of any faults identified by the device controller.

The signals may also be received at the remote controller and stored in the remote controller memory as part of a database. The remote controller and memory are configured to respectively access and store data from a plurality of radiotherapy machines connected to the remote controller via the network. The received signals may take a variety of forms. For example, signals may be received from both the first and second sensor on a regular basis. In this example, the first pump communicates the reading from the first sensor and the second pump communicates the reading from the second sensor to the device controller on a regular basis, for example every 4 seconds.

At step 330, the received signals are processed. The signals are processed in order to determine the nature of the fault in the radiotherapy device. This is in contrast with prior techniques, in which signals may be monitored to allow the existence of a fault to be identified, but the nature, i.e. cause, of the fault cannot be determined. Processing the received signals comprises establishing a first value and a second value, the first value being indicative of a pressure at the first end of the vacuum tube and the second value being indicative of a pressure at the second end of the vacuum tube, and comparing the first value with a first threshold and comparing the second value with a second threshold.

Establishing a value indicative of a pressure at the first or second end of the vacuum tube may comprise taking an average of signals received from the first or second sensor over a time period. For example, the time period may be a day, such that the first value is a daily average of signals received from the first sensor. Taking an average in this manner helps mitigate the impact of anomalies in the data, or changes in the sensor signals which are due to treatment taking place rather than being due to the fault.

Alternatively, establishing a value indicative of pressure at, for example, the first end of the vacuum tube may comprise taking a sensor signal received from the first sensor at a particular time. For example, the latest, i.e. most recent, sensor signal may be used as the first value. Alternatively, a sensor reading at a different particular time may be used, for example at a time during treatment when the machine output from the linear accelerator is at a maximum (as determined by, for example, a monitor chamber in the LINAC treatment head).

Establishing the second value may comprise identifying the worst signal reading from the second sensor in a given time period, for example during the previous day or week. The worst signal reading may represent when the vacuum in the region of the second end of the vacuum tube is at its lowest quality, and thus the worst sensor reading may be the lowest signal reading. This sensor reading/signal is then used as the second value. In this example, the corresponding first value is established as the signal reading at the first sensor at the same time as the worst signal reading at the second sensor. In another example, after the worst target vacuum signal value has been identified, a sample of signal values in the vicinity of this worst value is taken. For example, a sample of sensor signal values may be taken +/−30 minutes around the worst target vacuum value, and the signal values from the first sensor and the signal values from the second sensor may be respectively averaged in order to establish a first value indicative of a pressure at the first end of the vacuum tube and a second value indicative of a pressure at the second end of the vacuum tube. While an example of +/−30 minutes has been given, it will be appreciated that any suitable time period around the worst value may be used.

When a first value indicative of a pressure at the first end of the vacuum tube has been established, i.e. determined, and a second value indicative of a pressure at the second end of the vacuum tube has been established, i.e. determined, the first value is compared with a first threshold and the second value is compared with a second threshold. The second threshold is different to the first threshold. Treating the pressure signals from respective pumps/sensors connected with the vacuum tube differently is contrary to prior techniques, in which a combined signal (e.g. the mean of all signals) or each of the available signals is simply compared with a threshold safety value or an optimal vacuum threshold to determine whether the LINAC device vacuum is at an optimal level.

Analysis of data from machines showing a flight tube fault has suggested that, on such machines, the vacuum in the region of the flight tube is typically of reduced quality compared with the vacuum in the region of the electron gun.

In other words, the pressure in the vacuum tube is greater in a region proximate the flight tube than in a region proximate the electron gun. As such, sensor signals/readings at the target pump are typically greater than sensor signals/readings at the gun pump. Another way of phrasing this is that the vacuum quality in the region of the flight tube is typically reduced below a threshold, while the vacuum level in the region of the electron gun may still be acceptable. Therefore, comparing the second value with the second threshold may comprise determining that the second value is greater than the second threshold, and comparing the first value with the first threshold may comprise determining that the first value is less than the first threshold.

Somewhat counterintuitively, retrospective analysis of data from machines displaying a flight tube fault has indicated that if the gun pump, i.e. the first pump, registers more faults than the target pump, i.e. second pump, then the machine is likely to have a flight tube fault. Processing the signals at step 330 may therefore further comprise determining which of the gun or the target pump caused more faults to be registered over a set time period. A suitable time period is on the order of a day or a couple of days, or a week. For example, it may be determined that the gun pump registered more faults, i.e. fell below a safety or operating threshold, more often than the target pump during a one week time period.

In other words, processing the signals may comprise determining that the first pump has caused more faults to be registered than the second pump. In other words, the step may comprise determining that signals received from the first pump have more frequently fallen below a safety or operational threshold than signals received from the second pump.

At step 340, the nature of the fault is determined. At this stage, it is determined whether the fault is associated with the flight tube or not. The nature of the fault is determined based on the processing of the signals at step 330. The determination may be described as a determination of whether the fault is likely to be associated with the flight tube or not.

It has been found that a particularly effective way of determining that the nature of the fault is associated with the flight tube is to determine that the first value is lower than a first threshold and the second value is greater than a second threshold. The determination at step 340 may therefore be a simple process or algorithm whereby, if it is determined at step 330 that the first value is above the first threshold, and the second value is below the second threshold, then the nature of the fault is determined as being associated with the flight tube. If the received signals do not pass these conditions then this instead comprises determining that the fault is not associated with the flight tube.

The simple process or algorithm may be further based on whether or not signals received from the first pump have more frequently fallen below a safety or operational threshold than signals received from the second pump, as determined at step 330.

It has been found that a suitable first threshold, i.e. for the gun end pump, is a reading of −6.60 (1.06E-07 mBr) and a suitable second threshold, i.e. for the target end pump, is a reading of −6.25 (3.57E-07 mBar). In a specific embodiment using these thresholds, processing the signals at step 320 comprises determining a daily average of the first signals over a particular day to establish a first value, and determining an average of the second signals over the same day to establish a second value. If the second value is greater than −6.25 while the first value is less than −6.60, it is determined that the fault is associated with the flight tube.

While the step of receiving the signals has been identified and discussed in relation to step 320, it will be appreciated that in some embodiments signals are continuously received from the sensors, and in some embodiments the identification and notification of a fault may be based on signals received from the first and second sensor as the LINAC operates.

In a preferred embodiment, the device controller receives signals from the sensors and transmits them to the remote controller. The remote controller receives the signals at step 320 and then processes the signals at step 330 and determines the nature of the fault at step 340. However, at least some of the steps, and in some examples all of the steps, displayed in FIG. 3 may be performed on the device controller.

Figure 4:
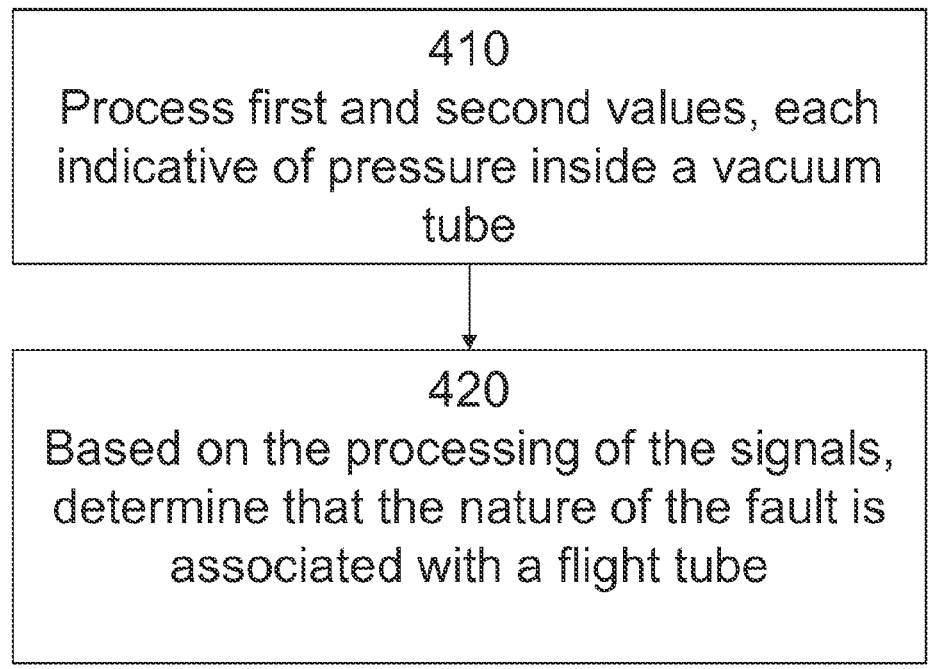
FIG. 4 depicts a method according to the present disclosure.

Reference is now made to the flowchart of FIG. 4. The method corresponds with the method depicted in FIG. 3 and described above, however the flowchart of FIG. 4 details the tasks which are performed by the remote controller 245, otherwise deemed the remote access controller.

At step 410, the first and second values are processed. Each value is indicative of pressure inside the vacuum tube and is calculated in the manner described above. As described above, the first and second values are derived from signals received from the first and second sensor and may be, for example, respective averages of signals received from the first and second sensors. The first and second value may be determined by any of the device controller, the central controller, or the remote controller. Processing the values comprises comparing the first value with a first threshold and comparing the second value with a second threshold. This step may be performed at any of the controller, but in a preferred embodiment is performed at the remote controller. In a preferred embodiment, comparing the second value with a second threshold comprises determining that the second value is greater than the second threshold, and comparing the first value with the first threshold comprises determining that the first value is less than the first threshold. The thresholds are different.

At step 420, based on the processing of the signals, it is determined whether or not the nature of the fault is associated with, e.g. caused by, the flight tube. As set out elsewhere herein, if the second value is above its threshold while the first value is below its threshold, then the fault is determined to be associated with the flight tube. As with the method of FIG. 4, there may be an additional step of outputting the nature of the fault in the radiotherapy device. Outputting the nature of the fault may comprise displaying an indication of the nature of the fault on a display screen. For example, the display may indicate that the fault either is, or isn't, associated with the flight tube. Alternatively or additionally, the method may comprise automatically issuing an alert identifying the nature of the fault to a field service engineer. The alert may comprise information identifying the machine at fault as well as the nature of the fault, along with information on recommended approaches to addressing and fixing the fault.

The above implementations have been described by way of example only, and the described implementations and arrangements are to be considered in all respects only as illustrative and not restrictive. It will be appreciated that variations of the described implementations and arrangements may be made without departing from the scope of the invention.

In an implementation, an additional step of checking whether the signals from either the first and/or the second sensor, or values derived from these signals, vary with the gantry rotation angle. In other words, an additional step of checking whether there appears to be any correlation between pressure inside the vacuum tube, as determined e.g. by signals from either the first or the second pump, and the angle to which the gantry has been rotated. For example, if there is a correlation, e.g. if the pressure values do vary with gantry angle by more than a threshold variance, then it is determined that the issue is not associated with the flight tube. This is because it has been determined that flight tube vacuum issues are not dependent on the angle to which the gantry has been rotated. Any available vacuum data, including any and all data types discussed herein, may be further investigated with respect to the gantry rotation value. In a simple example, gantry rotation angles can be split into 'bins', e.g. four bins between 0° and 90°, between 90° and 180°, between 180° and 270°, and between 270° and 360°. Vacuum signals received while the gantry was at these angles are processed. For example, an average target vacuum value and an average gun vacuum value can be determined for each bin. If any of the average values vary from each other by more than a threshold variance, it suggests that the vacuum level is dependent on the angle to which the gantry has been rotated. With a flight tube issue, it is not expected that gantry rotation will influence the vacuum. This is in contrast with other issues which may present themselves, for example a build-up of debris in the gun ion pump or the target ion pump, which do show fluctuations in vacuum values which are angle dependent.

In an implementation, processing the first value derived from signals from the first sensor and the second value derived from signals from the second sensor further comprises determining whether signals from the first sensor and/or signals from the second sensor are dependent on the rotation angle to which a gantry configured to hold a radiation source is rotated. Based on the determination, it can be determined whether the fault is associated with the flight tube. In an example, if the pressure inside the vacuum tube (i.e. the pressure signals, values, or vacuum level as determined using the pumps and sensors disclosed herein) varies with the gantry rotation angle above a threshold variance, then it is determined that the fault is not associated with, i.e. caused by, the flight tube. In some examples, if it is determined that the pressure inside the vacuum tube does not vary with the rotation angle above a threshold variance, then it is determined that the fault may still be associated with, i.e. caused by, the flight tube. In other words, determining that the pressure inside the vacuum tube varies with the rotation angle of a gantry to which the vacuum tube is attached means that the issue is unlikely to be associated with the vacuum tube. If the pressure inside the vacuum tube does not vary with the rotation angle, then other failure modes such as loose debris in the flight tube can be eliminated from consideration and the nature of the fault may still be associated with the flight tube.

Methods of the present disclosure allow a determination that the nature of a fault in a radiotherapy device, for example a clinical LINAC device, is associated with the flight tube. Prior techniques can identify that a LINAC machine has a fault, but cannot provide any further information which may assist a field service engineer. In contrast, the present methods allow both the identification of a fault, and a determination that the nature of the fault is associated with the flight tube. The present techniques therefore describe a cost-effective and efficient method of determining a fault.

The use of vacuum pumps in order to create a vacuum inside the vacuum tube of a LINAC is known in the art. Modern vacuum pumps are typically able to provide signals which indicate the pressure or level of vacuum in a vacuum tube. However, to date, these signals have simply been used in order to confirm that the requisite vacuum pressure inside the vacuum tube has been reached. To summarise the prior art methods, it is known to make use of signals from a LINAC device to determine: a) whether the requisite level of vacuum has been reached to allow optimal LINAC operation, and b) whether the level of vacuum has dipped below a certain level, for safety reasons and to ensure the LINAC continues to operate in an optimal manner. If the level of vacuum regularly drops below this vacuum 'safety' level, a fault may be registered.

However, the approach in the prior art to date to address the fault has been to send field service engineers to carry out diagnostic tests on the machine. As detailed herein, this prior technique is time consuming, inefficient and expensive. It has until now proved difficult to further specify the nature of a fault with the vacuum tube or pump system for a number of reasons. The quality of vacuum inside the vacuum tube can be affected by a large number of factors, for example due to thermal expansion of materials which form the various components of the vacuum tube, and small leaks can develop in a large number of regions of the vacuum tube. Further, several different possible faults may appear to manifest themselves in similar or identical ways, for example by reducing the quality of the vacuum in the vacuum tube. Possible components which could be degrading, or operating at non-optimal performance, and which may cause faults that are broadly associated with the vacuum system include one or more of the following components: the ion pump control units, either one of the gun or the target pump, contamination at the gun or target end of the vacuum tube, pinholes in either the RF input or output window, and loose/flexing connections between the components which form the vacuum tube. The issue is not that these components may degrade to a level which may compromise patient safety, as the vacuum is monitored to ensure patient safety at all times. However, once it has been determined that a fault exists which is broadly associated with the vacuum system it has to date proved difficult to identify which component is responsible.

The task is made additionally difficult as there are no sensors inside the waveguide or flight tube for the reasons given elsewhere herein, and it is therefore difficult to determine both whether there is a leak, and if there is then where it is located. Vacuum tests can be performed however this requires the radiotherapy machine to be taken out of service while a field service engineer conducts tests, for example using external probes. This is time consuming and costly to the maintenance provider and the hospital.

While it is possible to perform a leak test on the target window to confirm whether the nature of the fault is associated with the flight tube, many complicated component parts of the radiotherapy device must be disassembled before such a vacuum test may be performed. Depending on the model, the LINAC head (and the accompanying sensitive collimator and dosimetry system) may need to be removed from the device in order to provide access to the target window. This is a complicated and time consuming process, and one which without additional information is often considered a 'last resort' test. Various part replacements can be made in an attempt to address the fault before the flight tube is tested or replaced, which introduces cost and time inefficiencies. By way of an example, currently, when service engineers are sent out to investigate the cause of a vacuum fault, it is typical for it take between 60 and 100 hours of testing before it is determined that the nature/cause of the fault is associated with the flight tube.

By indicating to the field service engineer before he or she attends the machine that the flight tube is likely to be at fault, fewer ineffective solutions are attempted and fewer maintenance visits are needed.

At least some of the present techniques generally involve processing signals from sensors which provide signals indicative of pressure at different regions of the vacuum tube, and using the variation in signals to determine that an issue is likely associated with the flight tube of the LINAC device.

The approaches described above can also be applied to the detection of faults associated with the gun pump 230 and/or the target pump 234. Thus, another method of determining the nature of a fault in a radiotherapy device is provided. The radiotherapy device may comprise a linear accelerator and be configured to provide therapeutic radiation to a patient. The radiotherapy device may further comprise a vacuum tube comprising the electron gun 106 and a waveguide configured to accelerate electrons emitted by the electron gun 106 at a gun end of the vacuum tube toward a target end of the vacuum tube to produce said radiation. The radiotherapy device may further comprise a first vacuum pump—e.g., one of the gun pump 230 or the target pump 234—and a first sensor—e.g., one of sensors 232 or 236—configured to provide signals indicative of pressure inside the vacuum tube. The method may comprise processing a first value derived from signals from the first sensor, the first value being indicative of pressure inside the vacuum tube and, based on the processing of the signals, determining that the nature of the fault is associated with the first vacuum pump.

In some examples, the first value is indicative of pressure inside the vacuum tube at a first time, and the processing further comprises processing a second value from the signals from the first sensor, the second value being indicative of pressure inside the vacuum tube at a second time which is later than the first time, and comparing the second value to the first value.

In some examples, the radiotherapy device further comprises a second vacuum pump—e.g., the other of the gun pump 230 or the target pump 234—configured to provide a vacuum inside the vacuum tube, and a second sensor—e.g., the other of sensors 232 or 236. The first vacuum pump and the first sensor may be at one of the gun or target ends of the vacuum tube, and the second vacuum pump and the second sensor may be at the other of the gun or target ends of the vacuum tube. The processing may further comprise processing a third value from signals from the second sensor, the third value being indicative of pressure inside the vacuum tube at the first time, and processing a fourth value from the signals from the second sensor, the fourth value being indicative of pressure inside the vacuum tube at the second time which is later than the first time.

There are various indications that the gun pump 230 and/or the target pump 234 and/or the electron gun 106 is likely to have a fault, and these are set out in the below table. These indications can be used alone or in combination to determine that the nature of the fault is associated with the gun pump 230 and/or the target pump 234 and/or the electron gun 106.

| # | Indication | Comments | Component likely to be at fault |
|---|---|---|---|
| 1 | The first value is the same as (or 'equal to') a saturation value (e.g., the saturation value may be −6.94 in some radiotherapy devices, and −6.83 in other radiotherapy devices). The saturation value may be a best possible value or an ideal value, e.g., for the particular sensor used. | The pressure being at its best possible value suggests that there may be an issue with a monitoring circuit for the vacuum system, e.g. located inside the device controller. | Device Controller 240 |
| 2 | The first value is indicative of a pressure that is higher than a threshold (e.g., for a fault associated with the gun pump 230, −6.00 or −5.45; for a fault associated with the target pump 234, −6.05 or, when combined with indication 3, −6.15). | | First vacuum pump (gun pump 230/target pump 234). Could also be indictive of a vacuum leak at the related end of the system. |
| 3 | The second value is indicative of a higher pressure than the first value. In other words, the pressure is increasing over time; the vacuum is degrading. | | |
| 4 | The second value is the same as (or 'equal to') the first value. In other words, the pressure is constant. | In combination with indication 1, this is a strong indication that the gun pump 230 is at fault, since it is unlikely that the pressure would remain constant at its best possible value. | |
| 5 | The second value minus the first value is greater than the fourth value minus the third value. In other words, the pressure at one end of the vacuum tube is increasing faster than at the other end. | The vacuum degrading faster at one end of the vacuum tube than the other suggests that the vacuum pump at that end of the vacuum tube is likely to have a fault. | First vacuum pump (gun pump 230/target pump 234). Could also be indictive of a vacuum leak at the related end of the system. |
| 6 | A change over time in the pressure from the first sensor (e.g., the first and second values) is not correlated with a change over time in the pressure | | |

| # | Indication | Comments | Component likely to be at fault |
|---|---|---|---|
| | from the second sensor (e.g., the third and fourth values). | | |
| 7 | A change over time in the pressure does not constitute expected seasonal behaviour (based on historic pressure data, which may be stored in a database, and at least the first and second values). | | |
| 8 | The electron gun was replaced at or around the time of the first value. | This suggests that, instead of the gun pump 230 itself, the electron gun 106 is at fault and/or a vacuum leak has been introduced in the vicinity of the electron gun. | This indicates that a vacuum leak has been introduced where the electron gun is fitted, likely a poor seal. It could also be that a significant amount of contamination was introduced. |
| 9 | Indications 1 to 7 and the electron gun was not replaced at or around the time of the first value. | | First vacuum pump (gun pump 230/target pump 234) Could also be indictive of a vacuum leak at the related end of the system. |
| 10 | If the vacuum/pressure within the vacuum system shows a dependence on gantry angle. In other words, if the signals from one or more of the pressure sensors vary with the degree to which the vacuum system has been rotated around a patient by the gantry. | Pumps, in particular ion pumps, of the vacuum system can become contaminated and fill with debris as they operate. This debris can move around within the pump/system under the action of gravity, thus causing a dependence, or correlation, between pressure in the vacuum system and gantry rotation angle. If there are more than one pump connected/ coupled with the vacuum system, it is possible to isolate the fault to whichever pump signals exhibit this dependence. | Vacuum pump (in particular due to debris in the vacuum pump) |
| 11 | If the vacuum/pressure within the vacuum system shows a dependence on temperature. This can be determined via monitoring the dependence of pressure signals on the temperature of fluid in the device cooling system. | The material which comprises the vacuum system can expand and contract slightly with temperature, and thus vacuum leaks may present themselves at some temperature but not others. | Vacuum leak in the vacuum system. In systems with a first and a second pump, this indication can be used to diagnose a vacuum leak at a particular end of the system (gun or target) by determining which of the pump signals shows the dependence, or the greater dependence, on temperature. |
| 12 | If the vacuum pump signal changes when the machine energy changes from electron to x-ray or vice versa, or else if the vacuum pump signal shows a dependence on the beam mode of the machine (x-ray or electron). | The target mechanism is configured to move the target into and out from the path of the electron beam in order to switch the radiotherapy device from an X-ray beam (target in the path) or an electron beam (no target in the path of the beam) e.g. for the purpose of providing electron beam therapy. | Vacuum leak in the vicinity of the target mechanism. |

Figure 7:
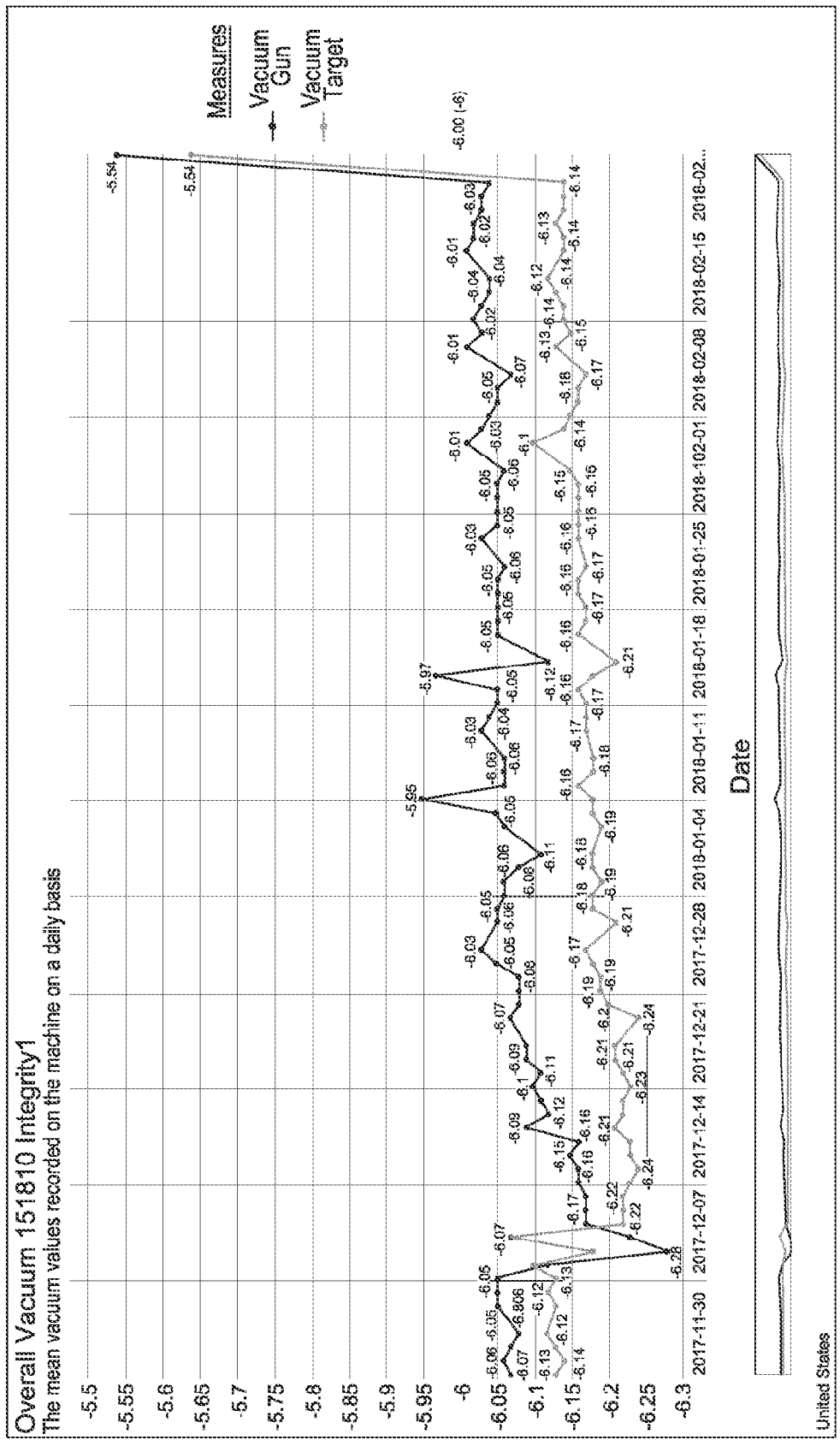
FIGS. 7 to 10 depict graphs showing vacuum values generated by a sensor according to the present disclosure.

FIG. 7 shows an example of indication 5, where the vacuum is degrading at both the gun and target ends, suggesting that neither the gun pump 230 nor the target pump 234 is at fault. Instead, the degradation on the right-hand side of the graph could be due to service work.

Figure 8:
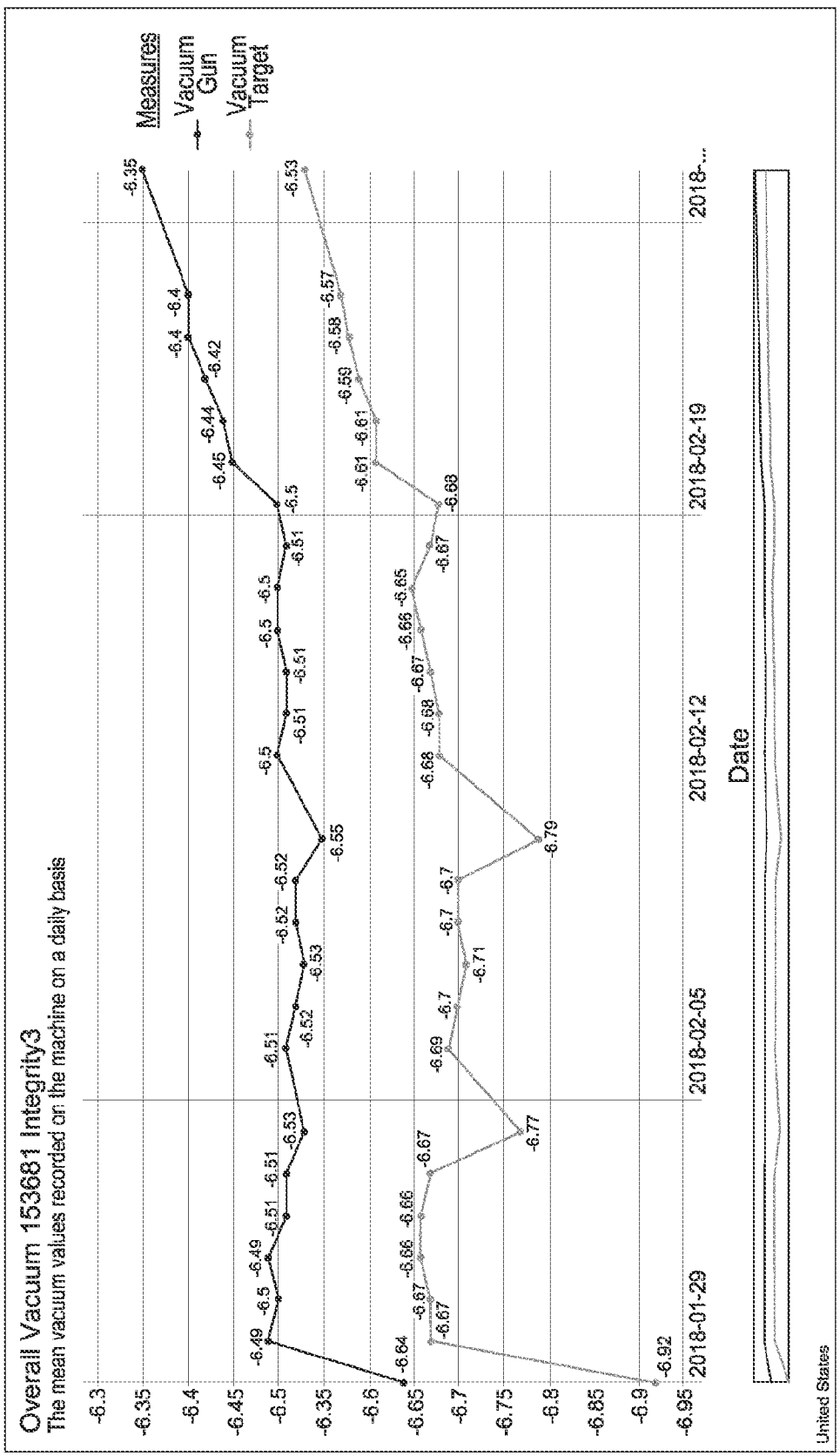

FIG. 8 shows an example of indications 3 and 6, where the pressure is degrading but the pressure at the target end follows the same trend as the pressure at the gun end. This suggests that neither the gun pump 230 nor the target pump 234 is at fault.

Figure 9:
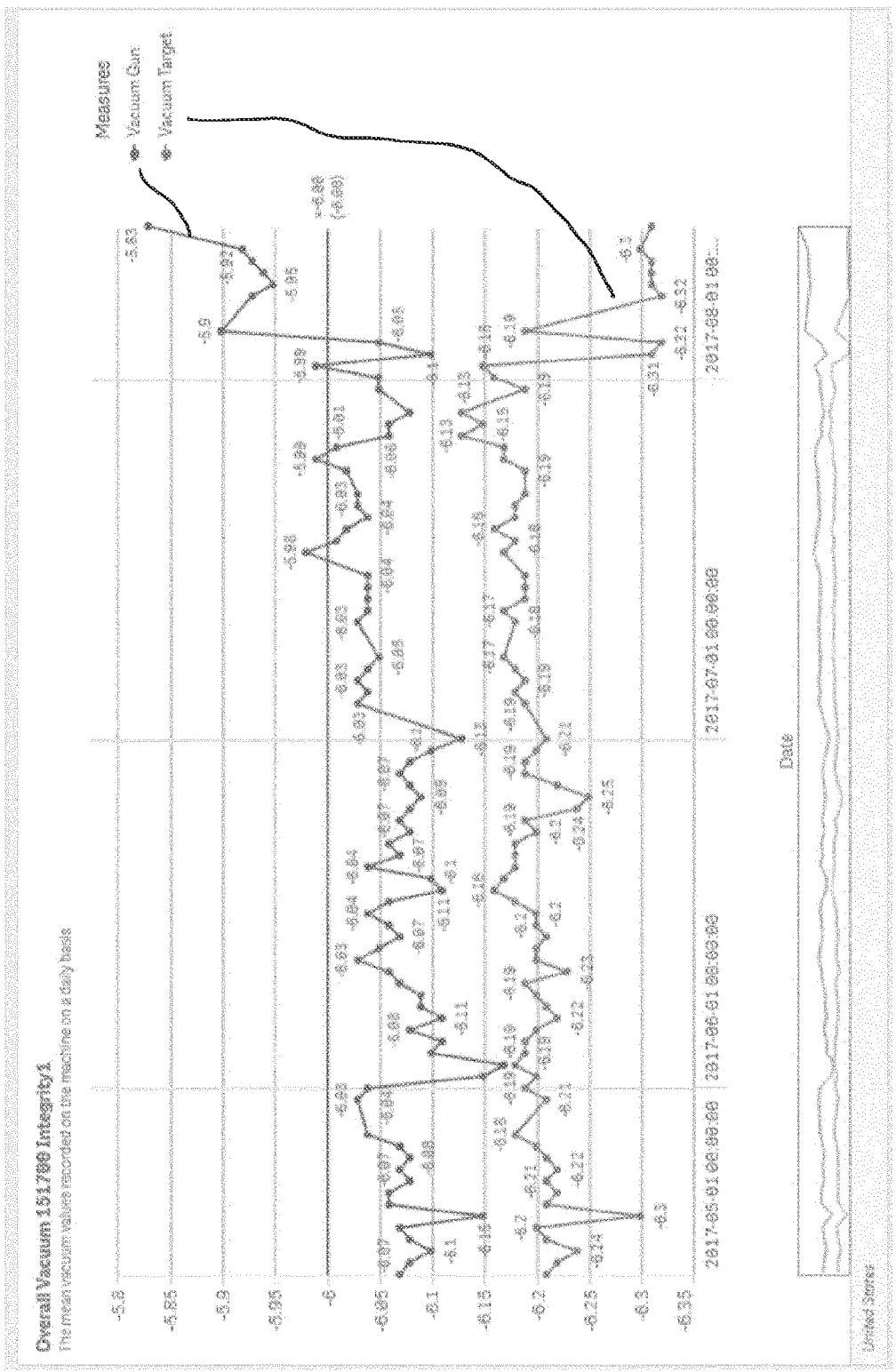

FIG. 9 shows another example of indication 6, where the pressure at the gun end has been degrading for the past few weeks, while the pressure at the target end has not followed the same trend. This suggests that There is a fault at the gun end of the vacuum system.

Figure 10:
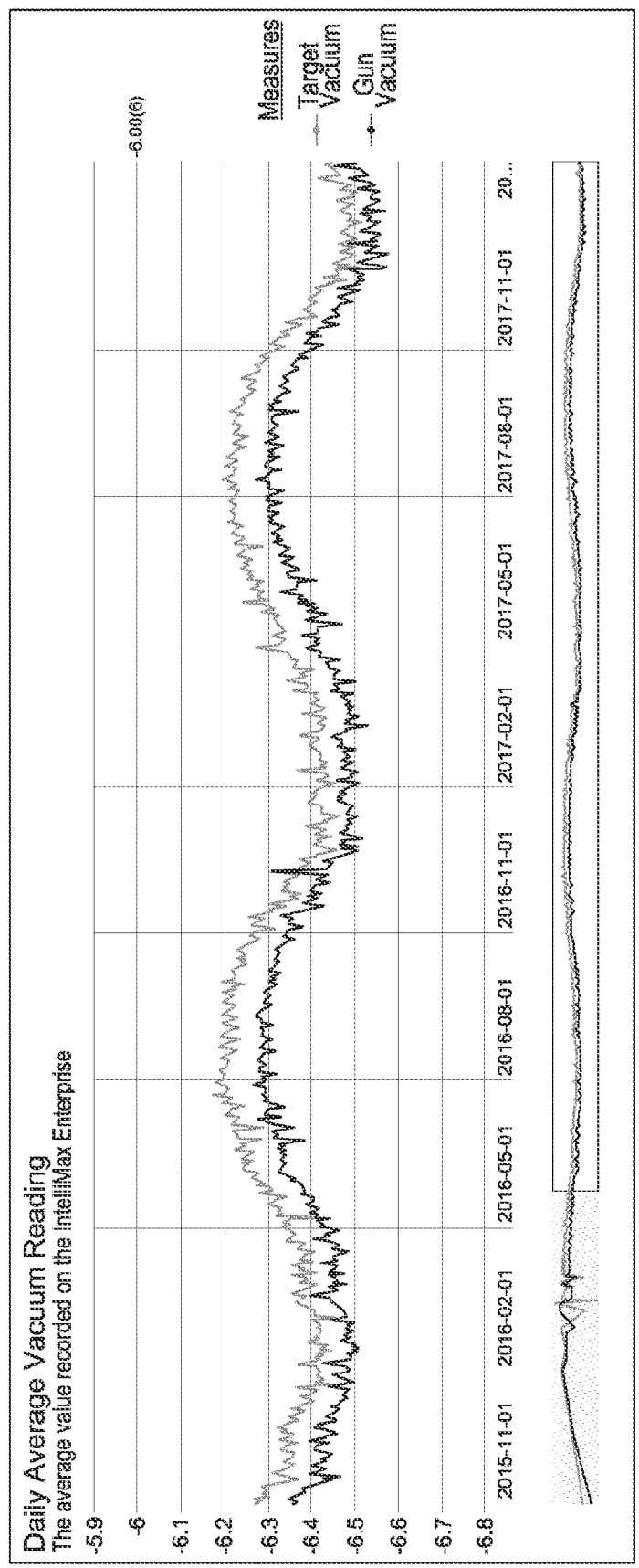

FIG. 10 shows an example of indication 7, where, although the most recent pressure measurements suggest one of the gun pump 230 or the target pump 234 is at fault, analysis of older (historic) pressure data shows that this is a seasonal trend and the pressure has not deviated from its normal value, given the season.

Disclosed herein is a method of determining the nature of a fault in a radiotherapy device, the radiotherapy device being configured to provide therapeutic radiation to a respective patient, the radiotherapy device comprising a linear accelerator comprising an electron gun and a vacuum tube through which electrons emitted by the electron gun are accelerated toward a target to produce said radiation, and a first and a second pressure sensor configured to provide signals indicative of pressure inside the vacuum tube, the first pressure sensor being configured to provide signals indicative of a pressure inside the vacuum tube proximate the electron gun and the second pressure sensor being configured to provide signals indicative of a pressure inside the vacuum tube proximate the target, the method comprising receiving a notification of a fault in the radiotherapy device, receiving a plurality of first signals from the first sensor of the radiotherapy device, and receiving a plurality of second signals from the second sensor of the radiotherapy device. The method also comprises processing the received signals, wherein processing the received signals comprises comparing each of the first signals to a first signal type threshold and comparing each of the second signals to a second signal type threshold. Based on the processing of the signals, the nature of the fault in the radiotherapy device is determined.

Also disclosed herein is a method of determining the nature of a fault in a radiotherapy device comprising a linear accelerator, the radiotherapy device being configured to provide therapeutic radiation to a patient, the radiotherapy device comprising an electron gun, a waveguide configured to accelerate electrons emitted by the electron gun toward a target to produce said radiation, and a flight tube; wherein the electron gun, waveguide and flight tube form a vacuum tube, the electron gun being located at a first end of the vacuum tube and the flight tube being located at a second end of the vacuum tube; and a first and a second sensor each configured to provide signals indicative of pressure inside the vacuum tube. The method comprises receiving signals from the first and second sensors, the first signals being processable to provide a first value indicative of pressure at the first end of the vacuum tube, and the second signals being processable to provide a second value indicative of pressure at the second end of the vacuum tube; processing the received signals, wherein processing the received signals comprises comparing the first value with a first threshold and comparing the second value with a second threshold; and based on the processing of the signals, determining that the nature of the fault is associated with the flight tube.

Examples of the present disclosure are set out in the following numbered clauses.

1. A method of determining the nature of a fault in a radiotherapy device comprising a linear accelerator, the radiotherapy device being configured to provide therapeutic radiation to a patient, the radiotherapy device comprising:
   a vacuum system comprising a vacuum tube comprising an electron gun and a waveguide configured to accelerate electrons emitted by the electron gun at a gun end of the vacuum tube toward a target end of the vacuum tube to produce said radiation;
   a first vacuum pump configured to provide a vacuum inside the vacuum tube; and
   a first sensor configured to provide signals indicative of pressure inside the vacuum tube;
   the method comprising:
   processing a first value derived from signals from the first sensor, the first value being indicative of pressure inside the vacuum tube; and
   based on the processing of the signals, determining that the nature of the fault is associated with the vacuum system.

2. The method of any preceding clause, wherein the vacuum system further comprises a device controller configured to receive signals from the first sensor, and wherein processing comprises comparing the first value to a saturation value.

3. The method of clause 2, wherein the processing comprises determining whether the first value is the same as a saturation value.

4. The method of clause 3, wherein the determining that the nature of the fault is associated with the vacuum system comprises determining that the fault is associated with the device controller responsive to determining that the first value is the same as the saturation value.

The diagnostic method of any of clauses 2-4 works because determining that the first value does not move with time away from a saturation value, which may simply be a constant value or else the 'ideal value' of a servomechanism, indicates that the device controller is at fault as it is unlikely that this is actually the case. This helps to rule out other failure modes such as debris or contamination in the vacuum system.

5. The method of clause 1, wherein determining that the nature of the fault is associated with the vacuum system comprises determining that the nature of the fault is associated with the first vacuum pump.

6. The method of any preceding clause, wherein the processing comprises determining whether the first value is indicative of the pressure inside the vacuum tube being higher than a threshold.

7. The method of clause 6, wherein the determining that the nature of the fault is associated with the first vacuum pump is responsive to determining that the first value is indicative of the pressure inside the vacuum tube being higher than the threshold.

8. The method of any preceding clause, wherein the first value is indicative of pressure inside the vacuum tube at a first time, and wherein the processing further comprises:
   processing a second value from the signals from the first sensor, the second value being indicative of pressure inside the vacuum tube at a second time which is later than the first time; and
   comparing the second value to the first value.

9. The method of clause 8, wherein comparing the second value to the first value comprises determining whether the second value is indicative of a higher pressure than the first value.

10. The method of clause 9, wherein the determining that the nature of the fault is associated with the first vacuum pump is responsive to determining that the second value is indicative of a higher pressure than the first value.

11. The method of any of clauses 8 to 10, wherein the determining that the nature of the fault is associated with the first vacuum pump is responsive to determining that the second value is the same as the first value.

12. The method of clause 11, wherein the determining that the nature of the fault is associated with the first vacuum pump is responsive to determining that the first and second values are the same as a saturation value.

13. The method of any of clauses 8 to 12, wherein the processing comprises determining, based on historic pressure data and at least the first and second values, whether a change over time in the pressure constitutes expected seasonal behaviour.

14. The method of any preceding clause, wherein the first vacuum pump and the first sensor are at one of the gun or target ends of the vacuum tube.

15. The method of clause 14, wherein the first vacuum pump and the first sensor are at the target end of the vacuum tube.

16. The method of clause 14, wherein the first vacuum pump and the first sensor are at the gun end of the vacuum tube.

17. The method of clause 16, wherein the first value is indicative of pressure inside the vacuum tube at a first time, and wherein the processing further comprises determining whether the electron gun was replaced at or around the first time.

18. The method of clause 17, wherein the processing further comprises determining whether the electron gun was replaced within a given period from the first time.

19. The method of any of clauses 17 to 18, wherein the determining that the nature of the fault is associated with the first vacuum pump is responsive to determining that the electron gun was not replaced at or around the first time.

20. The method of any preceding clause, the radiotherapy device further comprising:
a second vacuum pump configured to provide a vacuum inside the vacuum tube; and
a second sensor.

21. The method of clause 18, wherein the first sensor is configured to provide signals indicative of a pressure at a first region inside the vacuum tube, and the second sensor is configured to provide signals indicative of a pressure at a second region inside the vacuum tube.

22. The method of clause 21, wherein the first region is closer to one of the gun or target ends of the vacuum tube and the second region is closer to the other of the gun or target ends of the vacuum tube.

23. The method of any of clauses 20 to 22 when dependent on clause 13, wherein the second vacuum pump and the second sensor are at the other of the gun or target ends of the vacuum tube.

24. The method of any of clauses 20 to 23 when dependent on clause 8, wherein the processing further comprises:
processing a third value from signals from the second sensor, the third value being indicative of pressure inside the vacuum tube at the first time;
processing a fourth value from the signals from the second sensor, the fourth value being indicative of pressure inside the vacuum tube at the second time which is later than the first time;
determining, based on the first, second, third and fourth values, whether the pressure from the first sensor is increasing faster than the pressure from the second sensor.

25. The method of clause 24, wherein determining whether the pressure from the first sensor is increasing faster than the pressure from the second sensor comprises comparing a difference between the second and first values to a difference between the fourth and third values.

26. The method of any of clauses 24 to 25, wherein the determining that the nature of the fault is associated with the first vacuum pump is responsive to determining that the pressure from the first sensor is increasing faster than the pressure from the second sensor.

27. The method of any of clauses 24 to 26, wherein the processing further comprises determining, based on the first, second, third and fourth values, whether a change over time in the pressure from the first sensor is correlated with a change over time in the pressure from the second sensor.

28. The method of clause 27, wherein the determining that the nature of the fault is associated with the first vacuum pump is responsive to determining that the change over time in the pressure from the first sensor is not correlated with the change over time in the pressure from the second sensor.

29. The method of any preceding clause, wherein the first value is an average of signals received from the first sensor over a first time period.

30. The method of clause 29 when dependent on clause 8, wherein the second value is an average of signals received from the second sensor over a second time period, the second time period ending later than the first time period.

31. The method of any preceding clause, wherein the radiotherapy device comprises a gantry configured to rotate the vacuum system around a patient such that radiation can be directed toward the patient from multiple angles and/or directions around the patient; optionally wherein the radiotherapy device comprises a sensor or sensing apparatus configured to provide a signal indicative of the degree to which the gantry has been rotated.

32. The method of clause 31, further comprising receiving a gantry angle signal indicative of the degree to which the gantry has been rotated, optionally wherein the signal is received regularly.

33. The method of clause 32, wherein processing the first value comprises monitoring its dependence on the gantry angle signal and, if the first value shows a dependence on gantry angle, determining that the nature of the fault is associated with the first vacuum pump of the vacuum system, and optionally determining that the fault is associated with debris within the first pump.

34. The method of any of clauses 31 to 33, wherein the radiotherapy device comprises a second vacuum pump configured to provide a vacuum inside the vacuum tube and a second sensor, wherein the first sensor is configured to provide signals indicative of a pressure at a first region inside the vacuum tube, and the second sensor is configured to provide signals indicative of a pressure at a second region inside the vacuum tube, wherein the first region is closer to one of the gun or target ends of the vacuum tube and the second region is closer to the other of the gun or target ends of the vacuum tube, the method comprising processing signals received from both the first and the second sensor.

35. The method of clause 34, wherein processing signals received from both the first and the second sensor comprises monitoring their dependence on the gantry angle signal and, if the first values show a dependence on gantry angle whereas the second values do not, determining that the nature of the fault is associated with the first vacuum pump of the vacuum system, and optionally determining that the fault is associated with debris within the first pump.

This diagnostic process of clauses 31-35 is based on the idea that debris in the pumps moves under gravity, and hence the debris has a position which is dependent on gantry angle. This affects the ability of the pump to provide a vacuum. Identifying a dependence on gantry rotation angle indicates that the fault is unlikely to be associated with other failure modes such as vacuum leaks or faults associated with the controller/processor.

36. The method of any preceding clause, wherein the radiotherapy device comprises a fluid-based cooling system and a temperature sensor configured to provide a temperature signal indicative of the temperature of the fluid in the cooling system.

37. The method of clause 36, wherein processing the first value comprises monitoring its dependence on the temperature signal.

38. The method of clause 37, further comprising, if there is a dependence between the first value and the temperature signal, determining that the fault is associated with a vacuum leak in the first region of the vacuum system.

The diagnostic process of clauses 36-38 is based on the idea that vacuum leaks present themselves in different ways according to the temperature of the components which form the vacuum system. Identifying a dependence on temperature of the system indicates that the fault is unlikely to be associated with other failure modes such as debris in the pump, or faults associated with the controller/processor.

39. The method of any preceding clause, wherein the radiotherapy device comprises a target mechanism configured to move the target into, and out from, the path of the accelerated electrons such that the device can operate in a first beam therapy mode in which therapeutic x-rays are generated, and a second beam therapy mode in which the accelerated electrons form a beam of therapeutic electrons.

40. The method of clause 39, wherein processing the first value comprises monitoring its dependence on whether the target is in the path of the accelerated electrons or not.

41. The method of clause 40, further comprising, if there is a dependence between the first value and whether the target is in the path of the accelerated electrons or not, determining that the fault is associated with a vacuum leak in the region of the target mechanism.

42. The method of clause 40 or 41 further comprising, if the first value changes by a threshold amount when the target mechanism moves the target into, or out from, the path of the accelerated electrons, determining that the fault is associated with a vacuum leak in the region of the target mechanism.

The diagnostic process of clauses 39-42 is based on the idea that the change between beam modes (i.e. x-ray to electron or vice-versa) may introduce a vacuum leak. This is likely to be in the vicinity of the mechanical component which effects the change between beam modes, i.e. the target mechanism. The target mechanism may be referred to as the target actuation mechanism. This diagnostic process is particular effective if the vacuum system comprises two pumps in the manner described elsewhere herein, i.e. one pump configured to monitor signals in a first region of the system near the electron gun and a second pump configured to monitor signals in a second region of the system near the target. By determining that signals from the 'target pump' exhibit a dependence on whether or not the target is in the path of the beam or not, whereas signals from the 'gun pump' show no such dependence, it can be determined with further certainty that the leak is indeed associated with a vacuum leak in the region of the target mechanism.

43. The method of any preceding clause, further comprising receiving or generating a notification of a fault in the radiotherapy device.

44. The method of any preceding clause, further comprising outputting the nature of the fault in the radiotherapy device.

45. The method of clause 44, wherein outputting the nature of the fault comprises at least one of displaying an indication of the nature of the fault on a display screen and/or issuing an alert identifying the nature of the fault to a field service engineer.

46. A computer-readable medium comprising computer-executable instructions which, when executed by a processor of a device, cause the device to perform the method of any preceding clause.

47. Apparatus arranged to perform the method of any of clauses 1 to 45.

48. A system comprising a remote controller communicatively coupled to a central controller via a network, the central controller configured to receive data from a radiotherapy device, the radiotherapy device comprising a linear accelerator, the radiotherapy device being configured to provide therapeutic radiation to a patient, and the radiotherapy device comprising:
  a vacuum tube comprising an electron gun and a waveguide configured to accelerate electrons emitted by the electron gun at a gun end of the vacuum tube toward a target end of the vacuum tube to produce said radiation; and
  a first sensor configured to provide signals indicative of pressure inside the vacuum tube;
  the remote controller further being configured to:
  request and receive, from the central controller, a first value derived from signals from the first sensor; and
  perform the method of any of clauses 1 to 45.

The above implementations have been described by way of example only, and the described implementations and arrangements are to be considered in all respects only as illustrative and not restrictive. It will be appreciated that variations of the described implementations and arrangements may be made without departing from the scope of the invention.

The invention claimed is:

1. A method of determining a nature of a fault in a radiotherapy device, the radiotherapy device comprising a linear accelerator, the radiotherapy device being configured to provide therapeutic radiation to a patient, the radiotherapy device further comprising:
  a vacuum tube comprising an electron gun, a waveguide configured to accelerate electrons emitted by the electron gun toward a target to produce the therapeutic radiation, and a flight tube, the electron gun being located at a first end of the vacuum tube and the flight tube being located at a second end of the vacuum tube; and
  a first sensor and a second sensor, the first sensor being configured to provide a signal indicative of pressure at a first region inside the vacuum tube and the second sensor being configured to provide a signal indicative of pressure at a second region inside the vacuum tube, the first region being closer to the first end of the vacuum tube than the second region is;

the method comprising:
  processing a first value derived from the signal from the first sensor and a second value derived from the signal from the second sensor, the first value being indicative of pressure at the first region inside the vacuum tube, and the second value being indicative of pressure at the second region inside the vacuum tube, wherein processing the first value and second value comprises comparing the first value with a first threshold and comparing the second value with a second threshold; and
  based on the processing of the first value derived from the signal from the first sensor and processing the second value derived from the signal from the second sensor, determining that the nature of the fault is associated with the flight tube.

2. The method of claim 1, wherein comparing the second value with the second threshold comprises determining that the second value is greater than the second threshold.

3. The method of claim 1, wherein comparing the first value with the first threshold comprises determining that the first value is less than the first threshold.

4. The method of claim 1, wherein the first threshold and second threshold are different.

5. The method of claim 1, wherein the first value is an average of multiple signals received from the first sensor over a time period and the second value is an average of multiple signals received from the second sensor over the time period.

6. The method of claim 1, further comprising:
  deriving the first and second value based on the signal from the first and the signal second sensor.

7. The method of claim 1, further comprising:
  receiving a notification of a fault in the radiotherapy device.

8. The method of claim 1, further comprising:
  determining that the radiotherapy device has a fault by comparing the signal received from the first and the signal received from the second sensor with an operational threshold signal value, wherein the determining is made when at least one of the value of the signal received from the first sensor device or the value of the signal received from the second sensor device fall below the operational threshold value while the radiotherapy device is in operation.

9. The method of claim 1, further comprising:
  outputting the nature of the fault in the radiotherapy device.

10. The method of claim 9, wherein outputting the nature of the fault comprises at least one of: displaying an indication of the nature of the fault on a display screen or issuing an alert identifying the nature of the fault to a field service engineer.

11. The method of claim 1, wherein the radiotherapy device further comprises:
  a rotatable gantry to which a radiation source is attached, the radiation source being configured to provide the therapeutic radiation to a patient, wherein processing the first value and the second value further comprises determining that at least one of the first signal or the second signal are not dependent on a rotation angle of the gantry.

* * * * *